United States Patent [19]

Elkhoury et al.

[11] Patent Number: 5,589,480
[45] Date of Patent: Dec. 31, 1996

[54] TOPICAL APPLICATION OF OPIOID ANALGESIC DRUGS SUCH AS MORPHINE

[76] Inventors: George F. Elkhoury, 1561 Ramillo Ave., Long Beach, Calif. 90815; Christoph Stein, 310 Warren Ave., #302, Baltimore, Md. 21230

[21] Appl. No.: 291,614

[22] Filed: Aug. 17, 1994

[51] Int. Cl.⁶ .................................. A61K 31/485
[52] U.S. Cl. .................... 514/282; 424/DIG. 13; 514/817; 514/946; 514/947; 514/969
[58] Field of Search ................ 424/DIG. 13, 447, 424/448, 449; 514/946, 947, 817, 969

[56] References Cited

U.S. PATENT DOCUMENTS

| | | | |
|---|---|---|---|
| 3,275,510 | 9/1966 | Magid et al. | 514/946 |
| 4,416,886 | 11/1983 | Bernstein | 424/260 |
| 4,493,848 | 1/1985 | La Hann et al. | 514/946 |
| 4,626,539 | 12/1986 | Aungst et al. | 514/282 |
| 4,871,750 | 10/1989 | Roberts | 514/328 |
| 4,897,260 | 1/1990 | Ross et al. | 424/59 |
| 5,069,909 | 12/1991 | Sharma et al. | 424/499 |

OTHER PUBLICATIONS

Derwent Abstract of WO 9213540 Aug. 20, 1992, Parent et al.

Tennant et al, Abs. of Int. Pharm. Abs. (Lancet) v. 342 (Oct. 23, 1993) p. 1047–1048.

J. L. Joris et al., Anaesth. Analg., Opioid Analgesia At Perhipheral Sites: A Target for Opioids Released During Stress and Inflammation? 66:1277–81 (1987).

*Primary Examiner*—Shelley A. Dodson
*Attorney, Agent, or Firm*—Millen, White, Zelane, & Branigan, P.C.

[57] ABSTRACT

The present invention is directed to a method and apparatus for the topical application of opioid analgesic drugs such as morphine. Specifically, the present invention relates to a topical application of the opioid drug and specifically a morphine sulphate in a diluted solution to produce an analgesic effect in a localized area and typically in a localized inflamed area and without a transdermal migration of the opioid drug into the blood stream.

19 Claims, 1 Drawing Sheet

U.S. Patent      Dec. 31, 1996      5,589,480
FIG. 1
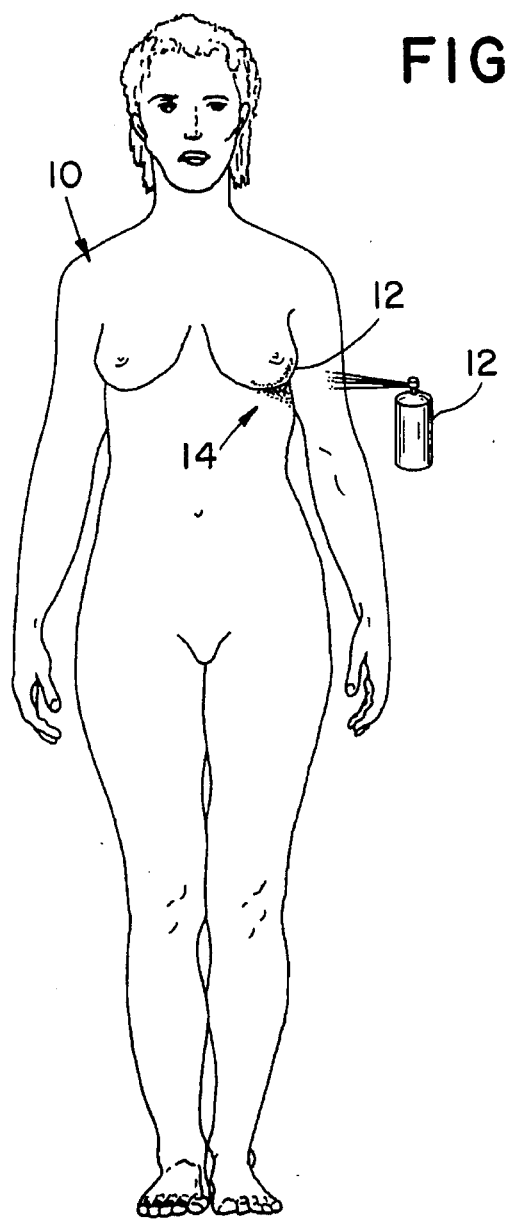
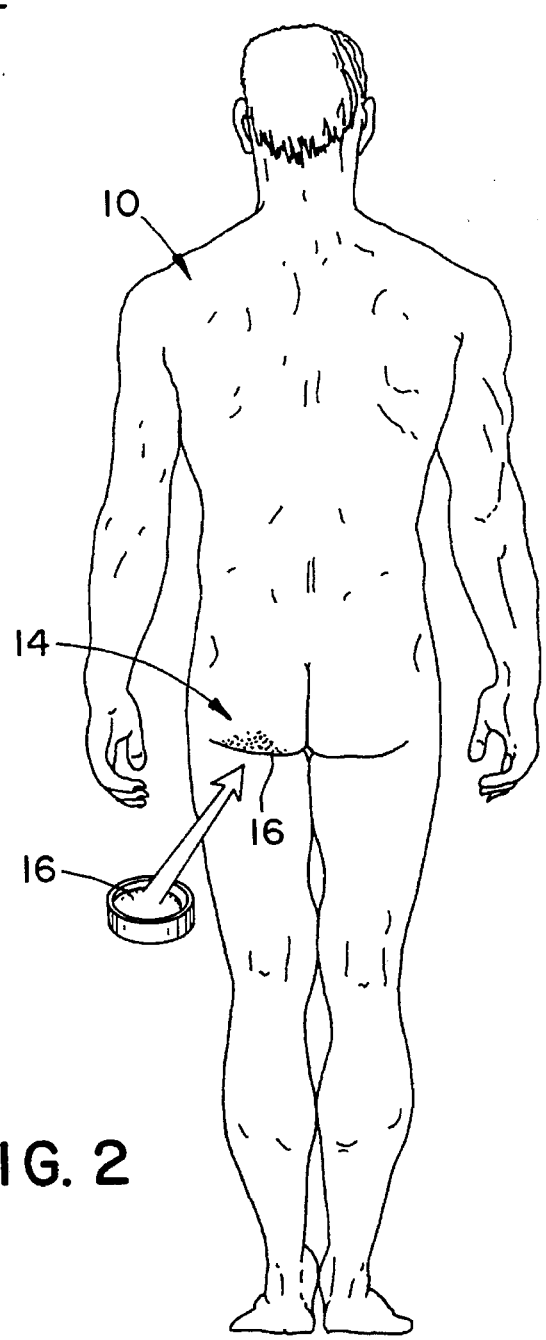
FIG. 2

TOPICAL APPLICATION OF OPIOID ANALGESIC DRUGS SUCH AS MORPHINE

BACKGROUND OF THE INVENTION

Morphine is the prototype of the class of opioid analgesic drugs which exert their effects by activating opioid receptors within the brain. When morphine is referred to individually in this application, this reference is meant to encompass other opioid drugs and is not meant to be morphine exclusively. Historically, narcotics have been used since the 18th century in the forms of oral or injectable morphine or opium in order to accomplish pain relief. Morphine is considered to be unsurpassed as an analgesic for severe pain.

Unfortunately, morphine and other opioid drugs have a number of severe side effects which hamper their wide spread use and acceptance by both physicians and patients. These side effects include: addiction, nausea, inhibition of breathing, somnolence and dysphoria, all of which are mediated by morphine's action within the brain. It is Still the current belief that narcotics ingested or injected will cross to the blood stream and from there go to the brain where there are morphine receptors. At that time, the narcotics are believed to attach to these morphine receptors and create a dullness of the pain but with all of the side effects described above. Of course, the worst potential effect is the addiction that can occur if the morphine is used beyond a few days or weeks on a continuous basis.

Because of the fear of addiction, the use of morphine as an analgesic has been restricted. In addition, major research efforts have been directed toward the development of morphine-like drugs that act within the brain but are devoid of the side effects. The market for these other drugs has never fully materialized because these drugs were not perceived as having the same analgesic properties of morphine and because typically these drugs were not produced to be both available in oral and injectable formats.

In the past ten years the intraspinal method of treating pain has been developed tremendously but, as more extensive use was made of this technique, a number of serious problems developed. The first problem is that the intraspinal method of treatment requires a spinal tap which of course necessitates the use of a needle to the spinal cord. The second problem results from the first in that if it is necessary to use the intraspinal method over a period of time, such as two or three weeks, medication must be injected into the spine for this period of time and the continuous needle sticks into the spine has potential hazards. Further, if it is necessary to use the intraspinal method over time, even though the dosage is substantially less compared to oral or intravenous dosages, there is still a high potential for addiction and with such addiction the resultant problems of withdrawal and its associated side effects.

Although intraspinal application of narcotics is still used to alleviate pain after surgery, this technique has the limitations with the potential for addiction as described above. In addition, it has been determined that with frail patients there is the risk that the patient can stop breathing and there have been a number of cases of respiratory arrest after the administration of narcotics using the intraspinal technique. Further, the intraspinal technique of administering narcotics creates difficulty with male patients and especially with elderly male patients in that there can be problems with urination and with consequent problems of urine retention. Finally, this intraspinal technique produces a problem of itching and the sequences of continuous itching can be debilitating.

In more recent studies it was discovered that opioid receptors may also be located in other peripheral tissues. This was reported in Stein C., Millan M. J., Shippenberg T. S., Herz A.: Peripheral effect of fentanyl upon nociception in inflamed tissue of the rat. *Neurosci Lett* 1988, 84:225–228 and in Stein C., Millan M. J., Yassouridis A., Herz A.: Antinociceptive effects of mu-and kappa-agonists in inflammation are enhanced by a peripheral opioid receptor-specific mechanism of action. *Eur J Pharmacol* 1988, 155:255–264. Subsequently, a large number of animal experiments were performed in Dr. Stein's laboratory, characterizing peripheral opioid receptors and their activation by morphine and other opioid drugs. This is reviewed in Stein C.: Peripheral mechanisms of opioid analgesia. *Anesth Analg* 1993, 76:182–191 and in Stein C., Lehrgerger K., Yassouridis A., Khoury G.: Opioids as novel intraarticular agents in arthritis. In: Progress in Pain Research and Management, ed. by Fields H. L., Liebeskind J. C. IASP Press, Seattle 1994, 1:289–296. A most important determination from these various studies is that the doses of the drugs required to produce analgesia in the peripheral tissues are extremely small and therefore devoid of the above mentioned side effects produced by dosages sufficient to operate on the brain.

In addition, it was determined that the endogenous ligands of peripheral opioid receptors (endorphines, the body's own pain killers) are located within the inflamed tissue. It was also determined that the endorphines can produce intrinsic analgesia within peripheral tissues both in animals and in humans (Stein Anesth. Analg. (1993) 182–191). A further determination was that the peripheral opioid effects are more pronounced in inflamed than in non-inflamed tissues.

SUMMARY OF THE INVENTION

Although there was a body of studies determining that opioid receptors were found in peripheral tissues and that peripheral opioid effects would be more pronounced in inflamed than in non-inflamed tissues, there was no specific determination of how to provide an analgesic effect, using narcotics such as morphine, other than by injection of morphine into a closed space such as a joint. The present invention is directed to a method and apparatus for a topical application of an opioid drug, such as morphine, for a direct activation of the peripheral opioid receptors on the surface of the skin without any substantial transdermal transmission of the opioid.

The fact that the opioid effects are more pronounced in inflamed than in non-inflamed tissues is a considerable advantage considering that most painful conditions are associated with inflammation, for example, cancer, arthritis, trauma, post-operative pain, skin lesions, etc. It has been determined in the present invention that extremely small systemically inactive doses of both conventional opioid drugs such as morphine and other opioids can produce potent analgesic effects after local application in peripheral tissue.

Initially, it was thought that it would be necessary to inject the morphine into an inflamed area since the inflammation activates the opioid receptors and it was also believed that the morphine had to be in an enclosed space to stay in contact with the area that was inflamed. The initial experiments were in conjunction with arthroscopic surgery of the knee and a number of patients were medicated after arthroscopic surgery with injected morphine. These patients were medicated either with morphine alone, with a local anesthetic such as Marcaine or a combination of Marcaine and 1 mg of morphine. It was shown that patients receiving morphine into the joint had significantly more pain relief than patients receiving the same dose intravenously (demonstrating a local effect) and that this effect was mediated by intraarticular opioid receptors. Furthermore, patients who received just Marcaine after the surgery had relief but the relief typically did not extend beyond 12 hours or at most the next day after surgery. The patients who received Marcaine plus one milligram of morphine in the knee had much better relief extending for at least twice as long as those that received Marcaine alone.

At this point, it was still thought that it was necessary to keep the morphine in a closed space, such as in a knee, and the results of such controlled clinical studies reporting analgesia produced by morphine injected into the knee joint were reported in Stein et al, N. Engl. J. Med., 325 (1991) 1123–1126; Comment in N. Engl. J. Med., 325 (1991) 1168–1169 and Khoury et al, Anesthesiology, 77 (1992) 263–266. These studies have been replicated by several other groups throughout the world, but this application of morphine was relatively restricted to the practice of orthopedic surgeons using the morphine injected into a joint after arthroscopic surgery and further progress was restricted because it was thought that the morphine had to be contained in the closed space so as to keep the medication in close contact with the inflamed area.

The first study of a patient using the topical application of an opioid drug, and specifically morphine, in accordance with the present invention occurred with a colostomy patient. Specifically, the patient had a severe infection around the colostomy on the skin and the skin was raw, red and inflamed to the degree that it was very difficult to change the dressing and clean the wound and the skin because of the severe pain involved. The patient was receiving 15 or 30 mg. IV morphine and still would be experiencing severe pain during a changing of the dressing.

Initially, it was thought that a morphine drip might dull the pain sufficiently so as to allow for a changing of the dressing and cleaning of the wound but because of the severe pain, it was determined to try a topical application of morphine. A very small quantity of morphine was mixed with Xylocane and was sprayed on the inflamed infectious area. The patient was not given any IV morphine before the changing of the dressing and the patient experienced excellent pain relief without any of the normal side effects of morphine. Because of the topical application of morphine, the nursing personnel were able to clean the wound in a very extensive way with relatively no pain for the patient and this was continued for almost a month in the hospital with daily use of the spray without any side effects and with excellent pain relief.

A second use of the topical application of morphine was with a series of patients who had burns from radiation therapy. For example, radiation therapy used for cancer of the breast quite often produces areas that are very sore and tender and are called "radiation therapy" burns. Other areas where radiation produces burns are in the buttocks when radiation therapy is used for cancer of the prostate. It was determined therefore to treat these various burns, which were created during radiation therapy, using a topical application of morphine such as through a morphine spray. A series of such patients were treated by using morphine alone diluted with a saline solution and with the morphine sprayed over the inflamed area. A very small amount of morphine such as two or three milligrams of morphine diluted with the saline was sprayed over the inflamed area.

All of the patients so treated reported excellent relief of pain and with the relief starting within 10–15 minutes of topical application. In addition, the relief lasted for at least 6 to 8 hours and up to 12 hours. This was significant since many of the patients reported that they were able to sleep a full night. This had theretofore been difficult because during sleep the patients would turn onto the burned area and awaken. The same experience was accomplished with patients who had pain on the tongue or in the mouth due to radiation burns.

One patient had severe burns on the buttocks due to prostate cancer and upon application of the spray, the patient had excellent relief of the pain. Prior to this time, the patient could not sit or lay on his back to do exercises because of the radiation burns. After the topical application of the morphine, the patient was able to sit for an hour and a half to do exercises and thereby maintain fitness.

After the series of patients who were tested who had radiation burns, other patients were tested who had skin burns from the sun. In these cases, we were able to alleviate the pain with less than one milligram of morphine, diluted and sprayed on the shoulder areas. Other patients who were helped were those who had acute shingles which would produce excruciating pain on the chest. This pain had not been relieved by any kind of narcotics but with the application of the morphine spray, typically three times a day, the patients reported that the pain had been significantly reduced and they were able to wear their clothing without hypersensitivity. The patients also typically healed faster with the use of the topical spray and, for example, after two or three days of using the spray, the healing process was rapidly advanced without any postherpetic neuralgia.

The above results were accomplished with the use of only two or three milligrams of the opioid drug, such as morphine, diluted to be sprayed or applied to a relatively large area of skin such as six inches square and without any side effects such as addiction, dullness in the brain, respiratory depression, nausea, vomiting or itching. All of this was accomplished without any significant absorption of the morphine into the blood stream since the morphine was merely applied topically to the skin without any transdermal agent.

In addition to the topical application of the opioid, such as morphine, using a spray, the opioid may be applied using a variety of different topical formulations such as gels, creams, etc. Depending upon the particular type of inflammatory skin lesion, the topical application will reduce pain in lesions such as sunburn, dermatitis, psoriasis, burn injuries, radiation burns, skin cancer, herpes zoster (shingles) or after skin grafts. The main advantage is the excellent pain relief without the typical side effects associated with oral or injectable narcotics. The potential for the present invention is widespread and the topical application opens up a whole new use of narcotics without the prior associated problems.

BRIEF DESCRIPTION OF THE DRAWINGS

FIG. 1 illustrates a topical application of an opioid drug, such as morphine, using a spray; and FIG. 2 illustrates a topical application of an opioid drug, such as morphine, using a cream or gel.

DETAILED DESCRIPTION OF THE DRAWINGS

FIG. 1 illustrates a method and apparatus of the present invention and specifically shows a patient 10 receiving a topical application of an opioid, such as morphine sulphate using a spray 12. In particular, a small quantity of the morphine sulphate solution is then sprayed onto an inflamed area 14 on a patient 10 to provide the particular pain relief described above. As a specific example, 90 milligrams of morphine sulphate may be diluted by 120 cc of saline to form the spray 12. The morphine sulphate is initially provided as a solution of 10 milligrams per cc so that final spray solution is 90 milligrams in a total of 129 cc. Thus, the final concentration of morphine in the spray is 0.69 milligrams per cc. The specific application may result in approximately 2 to 3 milligrams of morphine in solution to cover approximately a 6×6 square inch area.

FIG. 2 illustrates the same patient 10 with an inflamed area 14 and with an opioid, such as morphine sulphate applied topically in either a gel or a cream. As a specific example, 90 milligrams of morphine sulphate may be mixed with 120 cc of a topical gel such as K-Y gel. Again the morphine sulphate is initially provided in solution as 10 mg per cc and with the resultant mixture 16 being 90 mg of morphine sulphate in a total of 129 cc. The resultant set or cream is applied to the inflamed area 14 so that 2 to 3 mg of morphine sulphate covers an area of approximately 6×6 square inches.

In both methods of application as shown in FIGS. 1 and 2 the relief is substantial and with continued application on a periodic basis to continue this relief without any of the typical side effects such as addiction, nausea, inhibition of breathing, somnolence and dysphoria which would typically result if morphine were received by the brain. The quantities of the applied opioid described above are illustrative only and it is to be appreciated that lesser and greater quantities may be used. However, any quantity of opioid used in the topical application of the present invention is a small fraction of the typical dosage used in other methods of opioid treatment.

The following is a table of a representative sample of the results achieved with a number of patients listed as follows:

| | AGE | DISEASE | CAUSE | PAIN MEDS BEFORE TX | DESCRIPTION BEFORE TREATMENT |
|---|---|---|---|---|---|
| 1. | 69 | carcinoma of prostate | radiation therapy | Vicodin Darvocet | Blisters on buttocks with inability to sit for more than a few minutes. |
| 2. | 57 | carcinoma of cervix | radiation therapy | Vicodin Darvocet | Blisters on buttocks with inability to sit for more than a few minutes. |
| 3. | 73 | carcinoma of breast | radiation therapy | Vicodin Darvocet | Very sensitive breasts, whole breasts feel like they are pulling out. Can't sleep on right side. |
| 4. | 4 yr | tonsillectomy | surgery | n/a | unable to swallow for 3-4 days |
| 5. | 6 yr | tonsillectomy | surgery | n/a | unable to swallow for 3-4 days |
| 7. | 13 | third degree hot oil burn on right thigh | burn | none | applying ice on thigh |
| 8. | 28 | second degree sunburn of shoulders | sunburn | none | inability to wear lead apron at work. |
| 9. | 34 | shingles | acute Herpes Zooster | Vicodin × 2 Q 3 Hrs. | Severe pain. Unable to work, unable to sleep. |
| 10. | 64 | shingles on forehead | acute Herpes Zooster | Vicodin × 2 Q 3 Hrs. | Severe pain on forehead unrelieved with oral medication. |
| 11. | 81 | shingles of left leg | acute Herpes Zooster | Vicodin × 2 Q 3 hrs. | Severe pain left knee, like "on fire". Unable to bend knee. |

| | PRESCRIPTION | HOW MANY TIMES | DESCRIPTION AFTER TREATMENT |
|---|---|---|---|
| 1. | K-Y Jelly Morphine | 120 cc three times 90 mg | no pain at all, able to do bike exercises |
| 2. | K-Y Jelly Morphine | 120 cc every 6 hours 90 cc times 3 days | pain disappears |
| 3. | Saline Morphine | 120 cc every 6 hours 90 cc times 7 days | pain disappeared for six hours. Able to sleep all night on right side. |
| 4. | Saline Spray tonsil beds after surgery | 120 cc times one time | No pain after surgery. Able to swallow and eat ice cream same day. |
| 5. | Saline Spray tonsil beds after surgery | 120 cc times one time | No pain after surgery. Able to swallow and eat ice cream same day. |
| 6. | Saline Spray tonsil beds after surgery | 120 cc times one time | No pain after surgery. Able to swallow and eat ice cream same day. |
| 7. | Saline Morphine | 120 cc spray × 3 over 90 cc 3 hours. | Pain is gone. Complete healing over two days. |
| 8. | Saline Morphine | 120 cc spray × 2 over 90 cc 12 hours | Able to wear lead apron immediately. No Rx. needed. |
| 9. | Saline Morphine | 120 cc spray every 4 90 cc hours times 3 | Stopped all pain medication. Healed in three days. |
| 10. | K-Y Jelly Morphine | 120 cc every 6 hours 90 cc | 60%-70% of pain disappeared in one day, completely in 3-4 days. |

| 11. K-Y Jelly | 120 cc every 6 hours | Pain relieved 50% |
| Morphine | 90 cc | over 3 days. No |
| | | more pain medica- |
| | | tion needed. |

It is to be appreciated that all the present invention has been described primarily with reference to the use of morphine in the form of morphine sulphate. Other opioid analgesic drugs and other forms of morphine may be used to interact with the peripheral opioid receptors which are present in inflamed peripheral areas of the body and the invention is not to be limited specifically to morphine or morphine sulphate. It is also to be appreciated that other adaptations and modifications may be made and the invention is only to be limited by the appended claims Although the invention has been described with reference to a particular embodiment, it is to be appreciated that various adaptation and modifications may be made and the invention is only to be limited by the appended claims.

We claim:

1. A method of inducing analgesia in inflamed skin, comprising topically administering to a patient in need of such treatment a topically effective amount of an opioid analgesic agent, which amount is systemically ineffective for induction of analgesia, admixed with a pharmaceutically acceptable excipient for topical administration, whereby effective analgesia is induced in the substantial absence of transdermal delivery of the opioid analgesic agent to the systemic circulation.

2. A method of claim 1, wherein the opioid analgesic agent is administered in an amount analgesically equivalent to up to 3 mg of morphine per 6 $in^2$ of skin.

3. A method of claim 1, wherein the opioid analgesic agent is morphine.

4. A method of claim 3, wherein the morphine is in the form of morphine sulfate.

5. A method of claim 1, wherein the excipient is a liquid and the admixture is administered by spraying the liquid onto the skin.

6. A method of claim 1, wherein the excipient is a gel or cream and me admixture is administered by spreading the gel or cream on the skin.

7. A method of claim 1, wherein the amount administered is analgesically equivalent to 2–3 mg of morphine.

8. A pharmaceutical composition comprising an admixture of an opioid analgesic agent find a pharmaceutically acceptable excipient for topical administration to inflamed skin, wherein a unit dosage amount of the admixture contains a systemically ineffective amount of the opioid analgesic agent, and the excipient does not enhance transdermal systemic transmission of the opioid analgesic agent, with the proviso that, when the admixture is a liquid, it further comprises a component that is pharmaceutically unacceptable for systemic administration.

9. A pharmaceutical composition of claim 8, wherein a unit dosage amount of the opioid analgesic agent is analgesically equivalent to up to 3 mg per 6 $in^2$ of morphine.

10. A pharmaceutical composition method of claim 8, wherein the opioid analgesic agent is morphine.

11. A pharmaceutical composition method of claim 10, wherein the morphine is in the form of morphine sulfate.

12. A pharmaceutical composition method of claim 8, wherein the excipient is a liquid and the admixture is administered by spraying the liquid onto the skin.

13. A pharmaceutical composition method of claim 8, wherein the excipient is a gel or cream and the admixture is administered by spreading the gel or cream on the skin.

14. A pharmaceutical composition of claim 8, in a unit dosage fore analgesically equivalent to 2–3 mg of morphine.

15. A pharmaceutical composition comprising an admixture of an opioid analgesic agent and a pharmaceutically acceptable excipient for topical administration, wherein the excipient does not enhance transdermal systemic transmission of the opioid analgesic agent, in a unit dosage form analgesically equivalent to 2–3 mg of morphine.

16. A container adapted for spraying a measured amount of a liquid onto skin, and containing a pharmaceutical composition comprising an admixture of an opioid analgesic agent and a pharmaceutically acceptable excipient for topical administration.

17. A method of inducing analgesia in inflamed skin or mucosal tissue, comprising topically administering to a patient in need of such treatment a topically analgesically effective amount of an opioid analgesic agent, admixed with a pharmaceutically acceptable excipient for topical administration, wherein the amount of opioid analgesic is sufficient to directly activate peripheral opioid receptors but not sufficient to activate central nervous system opioid receptors.

18. A method of claim 1, wherein the inflamed skin is a herpetic lesion.

19. A method of claim 18, wherein the herpetic lesion is shingles.

* * * * *